(12) United States Patent
Jackson

(10) Patent No.: US 10,925,647 B2
(45) Date of Patent: Feb. 23, 2021

(54) THREADED CLOSURE WITH INWARDLY-FACING TOOL ENGAGING CONCAVE RADIUSED STRUCTURES AND AXIAL THROUGH-APERTURE

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 16/789,266

(22) Filed: Feb. 12, 2020

(65) Prior Publication Data

US 2020/0179014 A1    Jun. 11, 2020

Related U.S. Application Data

(63) Continuation of application No. 16/016,212, filed on Jun. 22, 2018, which is a continuation of application No. 15/883,993, filed on Jan. 30, 2018, now Pat. No. 10,004,541, which is a continuation of application No. 15/144,915, filed on May 3, 2016, now Pat. No. 9,907,577, which is a continuation of application No. 14/509,496, filed on Oct. 8, 2014, now abandoned, which is a continuation of application No. 13/694,970, filed on Jan. 23, 2013, now abandoned, which is a continuation of application No. 10/142,614, filed on May 9, 2002, now Pat. No. 8,377,100, which is a continuation-in-part of application No. 10/014,434, filed on Nov. 9, 2001, now Pat. No. 6,726,687.

(51) Int. Cl.
*A61B 17/70* (2006.01)
*A61B 17/68* (2006.01)
*A61B 90/00* (2016.01)

(52) U.S. Cl.
CPC ........ *A61B 17/7032* (2013.01); *A61B 17/685* (2013.01); *A61B 17/686* (2013.01); *A61B 17/7082* (2013.01); *A61B 17/7091* (2013.01); *A61B 2090/037* (2016.02)

(58) Field of Classification Search
CPC . A61B 17/685; A61B 17/686; A61B 17/7091; A61B 17/7032; A61B 2019/307
See application file for complete search history.

(56) References Cited

U.S. PATENT DOCUMENTS

| | | |
|---|---|---|
| 447,775 A | 3/1891 | Higbee |
| 1,300,275 A | 4/1919 | Johnson |
| 2,005,348 A | 6/1935 | Michell |
| 2,244,046 A | 6/1941 | Bradshaw |

(Continued)

FOREIGN PATENT DOCUMENTS

| | | |
|---|---|---|
| DE | 20207850 U1 | 10/2002 |
| EP | 1316294 A2 | 6/2003 |

(Continued)

*Primary Examiner* — Julian W Woo
(74) *Attorney, Agent, or Firm* — Polsinelli PC

(57) ABSTRACT

A closure for an open headed medical implant, such as a bone screw. The closure having a cylindrical body with an axis of rotation and also having a radially outer surface with a thread or other guide and advancement structure thereon. The body having a plurality of tool mating structures that communicate with a bottom surface of the body and that are parallel to but spaced from the axis of rotation.

15 Claims, 5 Drawing Sheets

(56) References Cited

U.S. PATENT DOCUMENTS

| | | | |
|---|---|---|---|
| D136,659 S * | 11/1943 | Janning et al. | D9/439 |
| 2,631,635 A | 3/1953 | Klooz | |
| 2,833,325 A | 5/1958 | Laisy | |
| 2,927,332 A | 3/1960 | Moore | |
| 3,419,058 A | 12/1968 | Walker | |
| 3,664,440 A | 5/1972 | Elenburg | |
| 3,963,304 A | 6/1976 | Suzuki | |
| 3,963,322 A | 6/1976 | Gryctko | |
| 3,977,221 A | 8/1976 | Foote | |
| 3,990,671 A | 9/1976 | Seyler | |
| 4,141,752 A | 2/1979 | Shipko | |
| 4,199,216 A | 4/1980 | Gryctko | |
| 4,210,374 A | 7/1980 | Churla | |
| 4,304,424 A | 12/1981 | Hansen | |
| 4,472,005 A | 9/1984 | Norton | |
| 4,492,500 A | 1/1985 | Ewing | |
| 4,528,874 A | 7/1985 | Dunn | |
| 4,538,947 A | 9/1985 | Burkholder | |
| 4,600,225 A | 7/1986 | Blose | |
| 4,627,759 A | 12/1986 | Kato | |
| 4,720,082 A | 1/1988 | Yang | |
| 4,764,068 A | 8/1988 | Crispell | |
| D309,664 S | 7/1990 | McGrane | |
| 5,005,562 A | 4/1991 | Cotrel | |
| 5,009,539 A | 4/1991 | Muellenberg | |
| 5,024,213 A | 6/1991 | Asher et al. | |
| 5,025,676 A | 6/1991 | Perretta | |
| 5,048,155 A | 9/1991 | Hwang | |
| 5,067,955 A | 11/1991 | Cotrel | |
| 5,073,074 A | 12/1991 | Corrigan et al. | |
| 5,092,635 A | 3/1992 | DeLange et al. | |
| 5,129,388 A | 7/1992 | Vignaud et al. | |
| 5,129,900 A | 7/1992 | Asher et al. | |
| 5,171,279 A | 12/1992 | Mathews | |
| 5,201,678 A | 4/1993 | Venezia | |
| 5,217,497 A | 6/1993 | Mehdian | |
| 5,234,430 A | 8/1993 | Huebner | |
| 5,244,323 A | 9/1993 | Tucchio | |
| 5,257,993 A | 11/1993 | Asher et al. | |
| D346,150 S | 4/1994 | Triantopoulos | |
| 5,334,203 A | 8/1994 | Wagner | |
| 5,366,330 A * | 11/1994 | Cosenza | B25B 13/065 |
| | | | 411/405 |
| 5,431,651 A | 7/1995 | Goble | |
| 5,443,467 A | 8/1995 | Biedermann et al. | |
| 5,474,555 A | 12/1995 | Puno et al. | |
| 5,476,464 A | 12/1995 | Metz-Stavenhagen et al. | |
| 5,487,744 A | 1/1996 | Howland | |
| 5,496,321 A | 3/1996 | Puno et al. | |
| 5,520,454 A | 5/1996 | Laing | |
| 5,533,912 A | 9/1996 | Fillinger | |
| 5,562,663 A * | 10/1996 | Wisnewski | A61B 17/7052 |
| | | | 606/250 |
| 5,605,458 A | 2/1997 | Bailey et al. | |
| 5,607,304 A | 3/1997 | Bailey et al. | |
| 5,628,740 A | 5/1997 | Mullane | |
| 5,662,650 A | 9/1997 | Bailey et al. | |
| 5,667,508 A | 9/1997 | Errico et al. | |
| 5,669,911 A | 9/1997 | Errico et al. | |
| 5,672,176 A | 9/1997 | Biedermann et al. | |
| 5,697,929 A | 12/1997 | Mellinger | |
| 5,727,314 A | 3/1998 | Ashcraft | |
| 5,733,286 A | 3/1998 | Errico et al. | |
| 5,752,957 A * | 5/1998 | Ralph | A61B 17/7037 |
| | | | 606/266 |
| 5,776,134 A | 7/1998 | Howland | |
| 5,782,833 A | 7/1998 | Haider | |
| 5,797,911 A | 8/1998 | Sherman et al. | |
| 5,848,913 A | 12/1998 | Ashcraft | |
| 5,870,934 A | 2/1999 | Cullinan | |
| 5,879,350 A | 3/1999 | Sherman et al. | |
| 5,882,350 A | 3/1999 | Ralph et al. | |
| 5,885,286 A | 3/1999 | Sherman et al. | |
| 5,941,885 A | 8/1999 | Jackson | |
| 5,954,725 A | 9/1999 | Sherman et al. | |
| 5,961,517 A | 10/1999 | Biedermann et al. | |
| 5,964,760 A | 10/1999 | Richelsoph | |
| 6,004,349 A | 12/1999 | Jackson | |
| 6,006,930 A | 12/1999 | Dreyer et al. | |
| 6,010,502 A | 1/2000 | Bagby | |
| 6,010,503 A | 1/2000 | Richelsoph et al. | |
| 6,053,917 A | 4/2000 | Sherman et al. | |
| 6,056,753 A | 5/2000 | Jackson | |
| 6,059,786 A | 5/2000 | Jackson | |
| 6,063,090 A | 5/2000 | Schlapfer | |
| 6,074,147 A | 6/2000 | Shu | |
| 6,074,391 A | 6/2000 | Metz-Stavenhagen et al. | |
| 6,076,437 A | 6/2000 | Saint Martin | |
| 6,077,262 A * | 6/2000 | Schlapfer | A61B 17/7032 |
| | | | 606/264 |
| 6,077,267 A | 6/2000 | Huene | |
| 6,102,913 A | 8/2000 | Jackson | |
| 6,110,172 A | 8/2000 | Jackson | |
| 6,113,601 A | 9/2000 | Tatar | |
| 6,135,321 A | 10/2000 | Hippensteel | |
| 6,146,383 A | 11/2000 | Studer et al. | |
| 6,158,996 A | 12/2000 | Becher | |
| 6,179,841 B1 | 1/2001 | Jackson | |
| 6,193,719 B1 | 2/2001 | Gournay | |
| 6,209,575 B1 | 4/2001 | Graziano | |
| 6,224,596 B1 | 5/2001 | Jackson | |
| 6,224,598 B1 | 5/2001 | Jackson | |
| 6,248,105 B1 | 6/2001 | Schlapfer et al. | |
| 6,254,146 B1 | 7/2001 | Church | |
| 6,261,288 B1 | 7/2001 | Jackson | |
| 6,280,442 B1 | 8/2001 | Barker et al. | |
| 6,296,642 B1 | 10/2001 | Morrison et al. | |
| 6,302,888 B1 | 10/2001 | Mellinger | |
| 6,355,040 B1 | 3/2002 | Richelsoph et al. | |
| 6,361,535 B2 | 3/2002 | Jackson | |
| 6,371,957 B1 | 4/2002 | Amrein et al. | |
| 6,412,831 B1 | 7/2002 | Noel et al. | |
| 6,440,137 B1 | 8/2002 | Horvath et al. | |
| 6,443,953 B1 | 9/2002 | Perra et al. | |
| 6,454,768 B1 | 9/2002 | Jackson | |
| 6,454,772 B1 | 9/2002 | Jackson | |
| 6,471,705 B1 | 10/2002 | Biedermann et al. | |
| 6,478,795 B1 | 11/2002 | Gournay | |
| 6,485,491 B1 * | 11/2002 | Farris | A61B 17/7002 |
| | | | 606/250 |
| 6,488,681 B2 | 12/2002 | Martin et al. | |
| 6,520,962 B1 | 2/2003 | Taylor et al. | |
| 6,550,959 B2 | 4/2003 | Huber | |
| 6,554,834 B1 | 4/2003 | Crozet et al. | |
| 6,565,565 B1 | 5/2003 | Yuan et al. | |
| 6,634,246 B2 | 10/2003 | Ohya | |
| 6,634,842 B2 | 10/2003 | Ueno | |
| 6,641,586 B2 * | 11/2003 | Varieur | A61B 17/7032 |
| | | | 411/403 |
| 6,688,921 B2 | 2/2004 | Borgstrom | |
| 6,699,248 B2 | 3/2004 | Jackson | |
| 6,730,089 B2 | 5/2004 | Jackson | |
| 6,764,354 B2 | 7/2004 | Kaine | |
| 6,783,527 B2 | 8/2004 | Drewry et al. | |
| 6,786,903 B2 | 9/2004 | Lin | |
| 6,788,756 B2 | 9/2004 | Erbes | |
| 6,817,910 B2 | 11/2004 | Borgstrom | |
| 6,835,196 B2 | 12/2004 | Biedermann et al. | |
| 6,837,889 B2 | 1/2005 | Shluzas | |
| 6,843,791 B2 | 1/2005 | Serhan | |
| 6,851,337 B2 | 2/2005 | Stokes | |
| 6,899,714 B2 | 5/2005 | Vaughan | |
| 6,997,927 B2 | 2/2006 | Jackson | |
| 7,087,057 B2 | 8/2006 | Konieczynski | |
| 7,096,071 B2 | 8/2006 | Ollivier | |
| 7,141,051 B2 | 11/2006 | Janowski | |
| 7,204,838 B2 | 4/2007 | Jackson | |
| 7,223,268 B2 | 5/2007 | Biedermann | |
| 7,232,104 B2 | 6/2007 | Krapels | |
| 7,247,020 B2 | 7/2007 | Takahashi | |
| 7,250,052 B2 | 7/2007 | Landry et al. | |
| 7,311,563 B2 | 12/2007 | Siebens | |
| 7,320,570 B2 | 1/2008 | Czarnek | |
| 7,334,307 B1 | 2/2008 | Helenowski | |

(56) References Cited

U.S. PATENT DOCUMENTS

| | | |
|---|---|---|
| 7,490,394 B2 | 2/2009 | Zakrzewski |
| 7,515,220 B2 | 4/2009 | Ko et al. |
| 7,566,163 B2 | 7/2009 | Inoue |
| 7,591,839 B2 | 9/2009 | Biedermann et al. |
| 7,604,655 B2 | 10/2009 | Warnick |
| 7,611,518 B2 * | 11/2009 | Walder ............... A61B 17/704 606/246 |
| 7,641,674 B2 | 1/2010 | Young |
| 7,662,172 B2 | 2/2010 | Warnick |
| 7,686,835 B2 | 3/2010 | Warnick |
| 7,717,942 B2 | 5/2010 | Schumacher |
| 7,717,943 B2 | 5/2010 | Kirschman |
| 7,766,945 B2 | 8/2010 | Nilsson et al. |
| 7,794,477 B2 | 9/2010 | Melkent et al. |
| 7,857,834 B2 | 12/2010 | Boschert |
| 7,972,364 B2 | 7/2011 | Biedermann et al. |
| 8,092,494 B2 | 1/2012 | Butler et al. |
| 8,162,989 B2 | 4/2012 | Khalili |
| 8,377,100 B2 | 2/2013 | Jackson |
| 8,382,809 B2 | 2/2013 | Kaufman et al. |
| 8,439,922 B1 | 5/2013 | Arnold et al. |
| 8,801,761 B2 | 8/2014 | Kirschman |
| 8,814,913 B2 | 8/2014 | Jackson |
| 8,828,060 B2 | 9/2014 | Biedermann et al. |
| 8,840,349 B2 * | 9/2014 | Mevius ............... B25B 13/06 411/410 |
| 8,911,479 B2 | 12/2014 | Jackson et al. |
| 8,998,956 B2 | 4/2015 | George |
| 9,068,587 B2 | 6/2015 | Sage et al. |
| 9,445,847 B2 | 9/2016 | Biedermann et al. |
| 9,636,146 B2 | 5/2017 | Jackson et al. |
| 9,717,533 B2 | 8/2017 | Jackson et al. |
| 9,743,957 B2 | 8/2017 | Jackson |
| 9,861,394 B2 | 1/2018 | Jackson |
| 10,004,541 B1 | 6/2018 | Jackson |
| 10,206,716 B2 | 2/2019 | Jackson et al. |
| 2001/0047208 A1 | 11/2001 | Michelson |
| 2002/0035366 A1 | 3/2002 | Walder et al. |
| 2002/0120272 A1 | 8/2002 | Yuan |
| 2002/0133154 A1 | 9/2002 | Saint Martin |
| 2002/0143341 A1 | 10/2002 | Biedermann et al. |
| 2002/0173791 A1 | 11/2002 | Howland |
| 2003/0014054 A1 | 1/2003 | Huebner |
| 2003/0023243 A1 | 1/2003 | Biedermann et al. |
| 2003/0088248 A1 | 5/2003 | Reed |
| 2003/0100896 A1 | 5/2003 | Biedermann et al. |
| 2003/0100904 A1 | 5/2003 | Biedermann |
| 2003/0114852 A1 | 6/2003 | Biedermann et al. |
| 2003/0125741 A1 | 7/2003 | Biedermann et al. |
| 2003/0149431 A1 | 8/2003 | Varieur et al. |
| 2003/0153913 A1 | 8/2003 | Altarac et al. |
| 2003/0158552 A1 | 8/2003 | Jeon et al. |
| 2003/0187433 A1 | 10/2003 | Lin |
| 2003/0199873 A1 | 10/2003 | Richelsoph |
| 2004/0039383 A1 | 2/2004 | Jackson |
| 2004/0049196 A1 | 3/2004 | Jackson |
| 2004/0138660 A1 | 7/2004 | Serhan |
| 2004/0138662 A1 | 7/2004 | Landry et al. |
| 2004/0143265 A1 | 7/2004 | Landry |
| 2004/0147929 A1 | 7/2004 | Biedermann et al. |
| 2004/0153068 A1 | 8/2004 | Janowski et al. |
| 2004/0167524 A1 | 8/2004 | Jackson |
| 2004/0167525 A1 | 8/2004 | Jackson |
| 2004/0172032 A1 | 9/2004 | Jackson |
| 2004/0176766 A1 | 9/2004 | Shluzas |
| 2004/0186474 A1 | 9/2004 | Matthis et al. |
| 2004/0260283 A1 | 12/2004 | Wu et al. |
| 2005/0131421 A1 | 6/2005 | Anderson et al. |
| 2005/0182410 A1 | 8/2005 | Jackson |
| 2005/0216003 A1 | 9/2005 | Biedermann et al. |
| 2005/0277928 A1 | 12/2005 | Boschert |
| 2005/0283157 A1 | 12/2005 | Coates et al. |
| 2006/0009773 A1 | 1/2006 | Jackson |
| 2006/0036244 A1 | 2/2006 | Spitler et al. |
| 2006/0079893 A1 | 4/2006 | Jackson |
| 2006/0083603 A1 | 4/2006 | Jackson |
| 2006/0089643 A1 | 4/2006 | Mujwid |
| 2006/0155278 A1 | 7/2006 | Warnick |
| 2007/0043357 A1 | 2/2007 | Kirschman |
| 2007/0093827 A1 | 4/2007 | Warnick |
| 2007/0123862 A1 | 5/2007 | Warnick |
| 2007/0123867 A1 | 5/2007 | Kirschman |
| 2007/0208344 A1 | 9/2007 | Young |
| 2007/0219554 A1 | 9/2007 | Landry et al. |
| 2007/0260246 A1 | 11/2007 | Biedermann |
| 2007/0270832 A1 | 11/2007 | Moore |
| 2008/0015596 A1 | 1/2008 | Whipple |
| 2008/0039848 A1 | 2/2008 | Jackson |
| 2008/0045953 A1 | 2/2008 | Garamszegi |
| 2008/0071277 A1 | 3/2008 | Warnick |
| 2008/0086131 A1 | 4/2008 | Daly et al. |
| 2008/0097457 A1 | 4/2008 | Warnick |
| 2008/0167689 A1 | 7/2008 | Matthis et al. |
| 2008/0215100 A1 | 9/2008 | Matthis et al. |
| 2008/0249576 A1 | 10/2008 | Hawkes et al. |
| 2008/0269809 A1 | 10/2008 | Garamszegi |
| 2008/0292429 A1 | 11/2008 | Hasenbohler et al. |
| 2009/0093844 A1 | 4/2009 | Jackson |
| 2009/0138052 A1 | 5/2009 | Biedermann et al. |
| 2009/0221879 A1 | 9/2009 | Gorek |
| 2010/0004692 A1 | 1/2010 | Biedermann et al. |
| 2010/0036417 A1 | 2/2010 | James et al. |
| 2010/0057126 A1 | 3/2010 | Hestad |
| 2010/0125302 A1 | 5/2010 | Hammill, Sr. et al. |
| 2010/0174319 A1 | 7/2010 | Jackson |
| 2011/0152947 A1 | 6/2011 | Kirschman |
| 2011/0208248 A1 | 8/2011 | Barrus et al. |
| 2011/0270321 A1 | 11/2011 | Prevost et al. |
| 2012/0029578 A1 | 2/2012 | Suh |
| 2013/0013003 A1 | 1/2013 | Carbone et al. |
| 2014/0052187 A1 | 2/2014 | McBride et al. |
| 2014/0081334 A1 | 3/2014 | Jackson |
| 2014/0142633 A1 | 5/2014 | Jackson et al. |
| 2014/0214097 A1 | 7/2014 | Jackson et al. |
| 2015/0119942 A1 | 4/2015 | Jackson et al. |
| 2015/0148846 A1 | 5/2015 | Jackson |
| 2015/0164558 A1 | 6/2015 | Jackson et al. |
| 2016/0038188 A1 | 2/2016 | Jackson et al. |
| 2016/0242818 A1 | 8/2016 | Jackson |
| 2017/0189073 A1 | 7/2017 | Jackson et al. |
| 2017/0333083 A1 | 11/2017 | Jackson et al. |
| 2017/0354441 A1 | 12/2017 | Jackson et al. |
| 2017/0354443 A1 | 12/2017 | Jackson |
| 2018/0243013 A1 | 8/2018 | Jackson et al. |
| 2018/0296249 A1 | 10/2018 | Jackson |
| 2019/0175225 A1 | 6/2019 | Jackson et al. |
| 2019/0231400 A1 | 8/2019 | Jackson et al. |
| 2019/0274734 A1 | 9/2019 | Jackson et al. |
| 2019/0298415 A1 | 10/2019 | Jackson et al. |
| 2020/0163702 A1 | 5/2020 | Jackson et al. |

FOREIGN PATENT DOCUMENTS

| | | |
|---|---|---|
| EP | 1570796 A1 | 9/2005 |
| GB | 2140523 A | 11/1984 |
| WO | WO 95/13755 | 5/1995 |
| WO | WO 02/076314 | 10/2002 |

\* cited by examiner

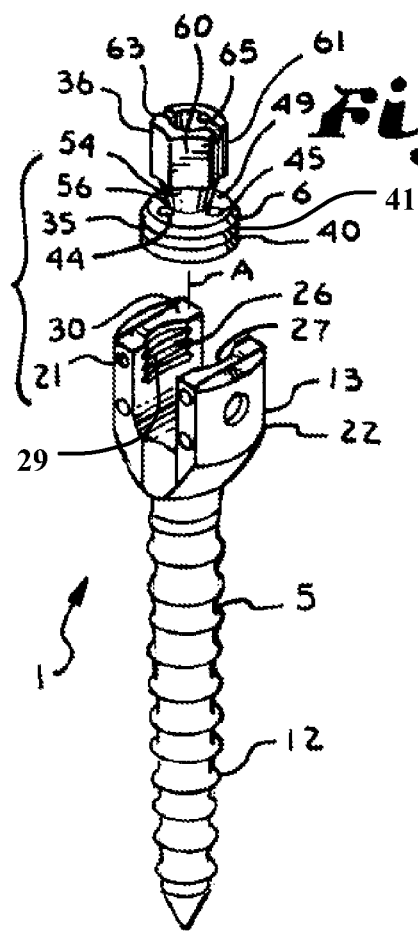
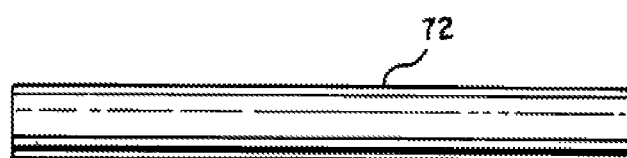
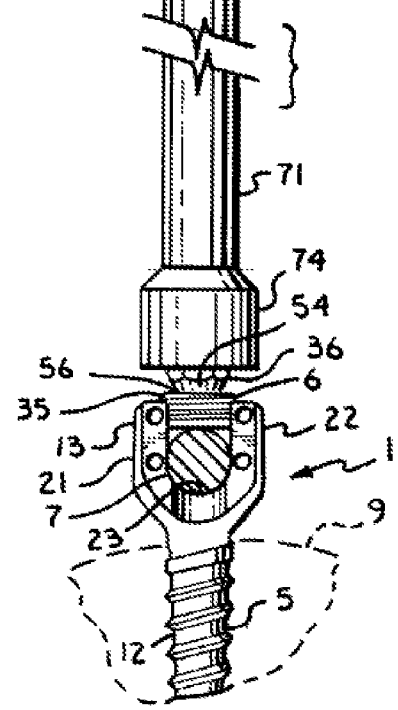
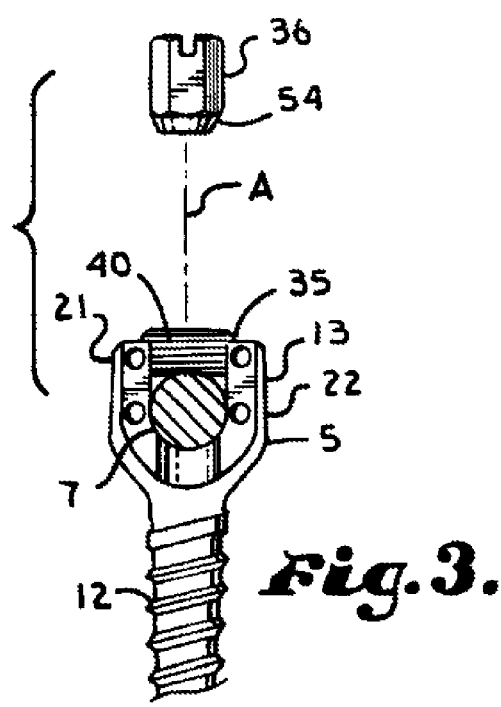

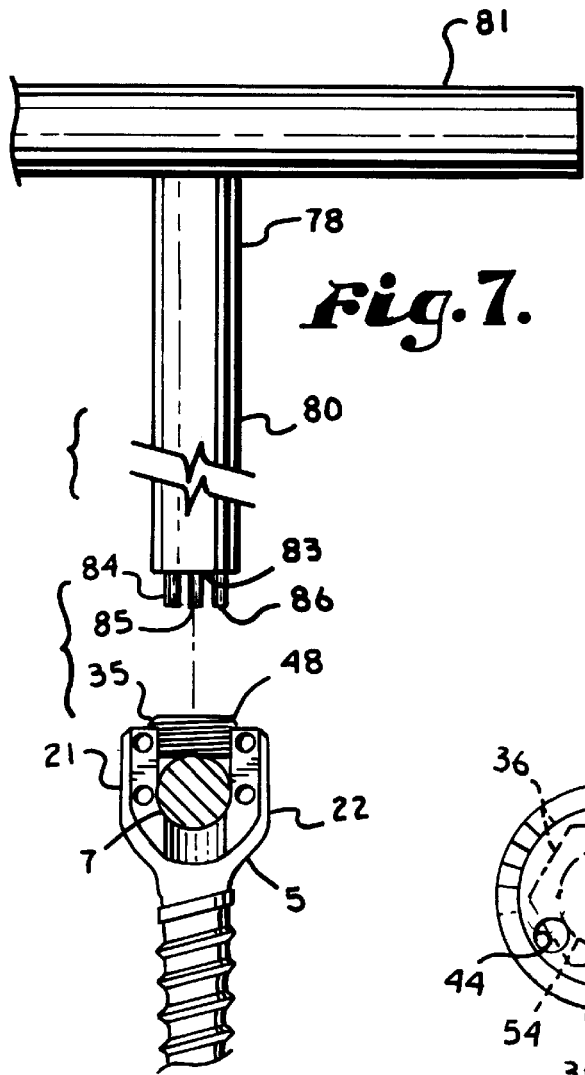
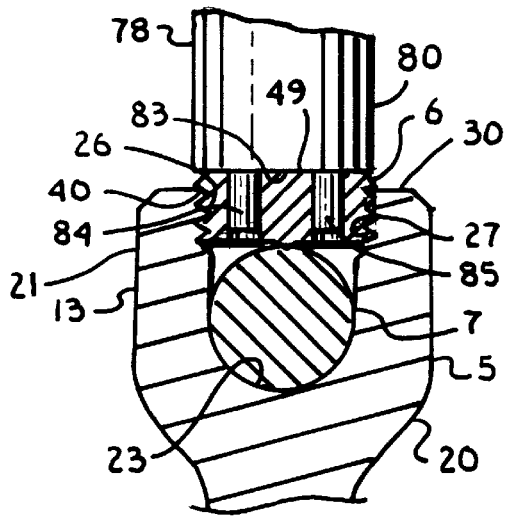
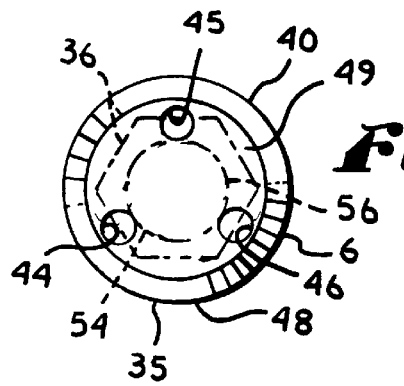
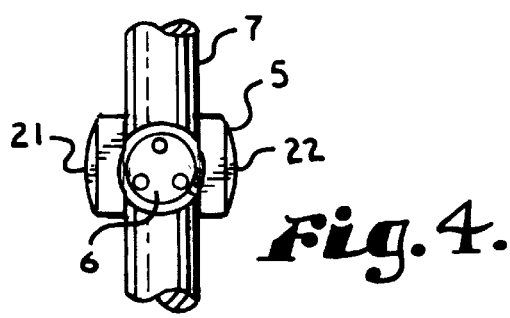
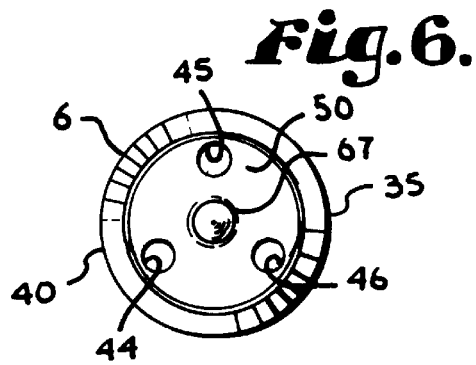

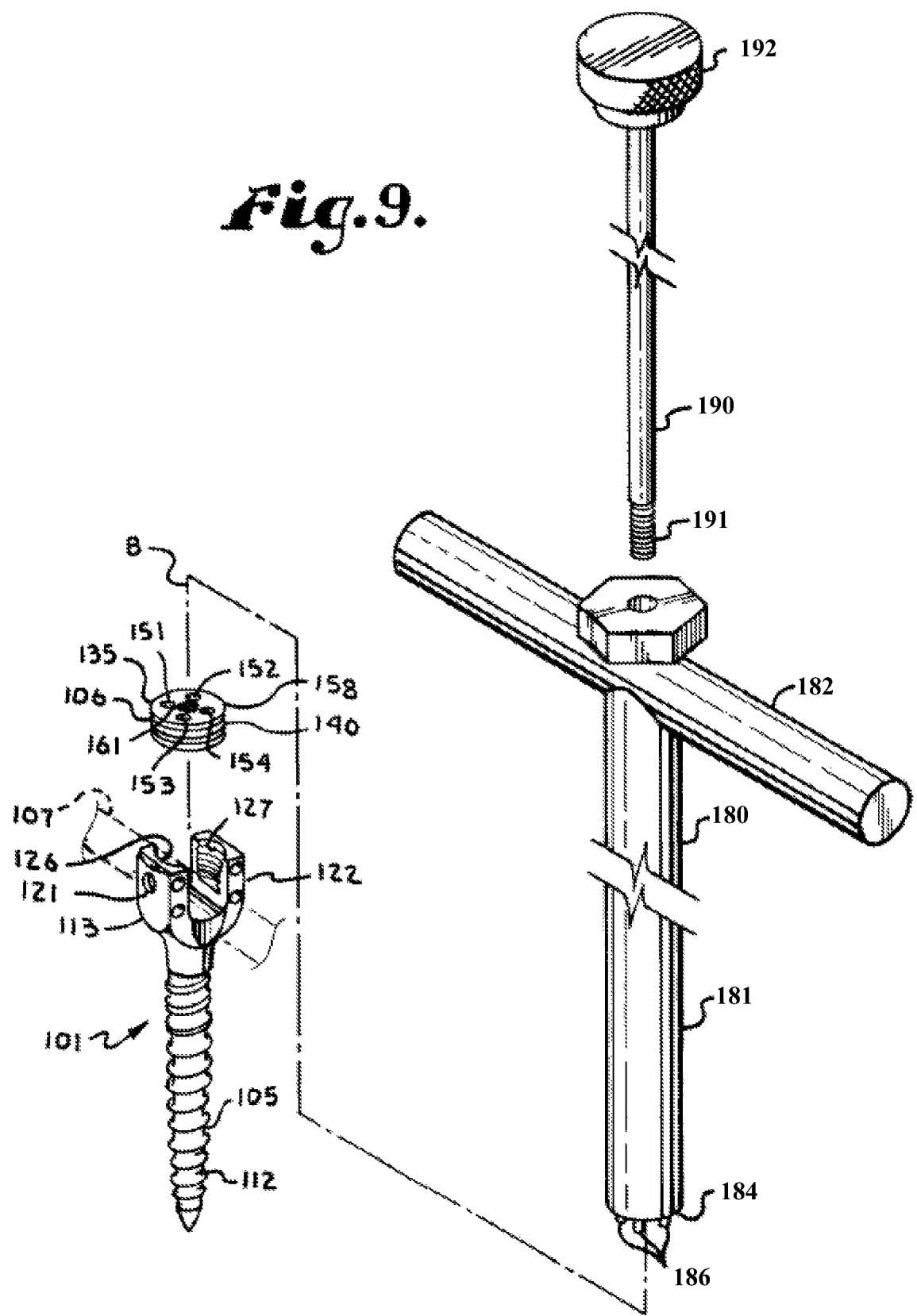

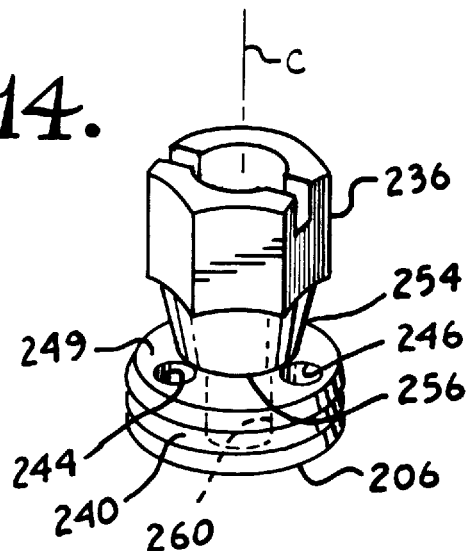
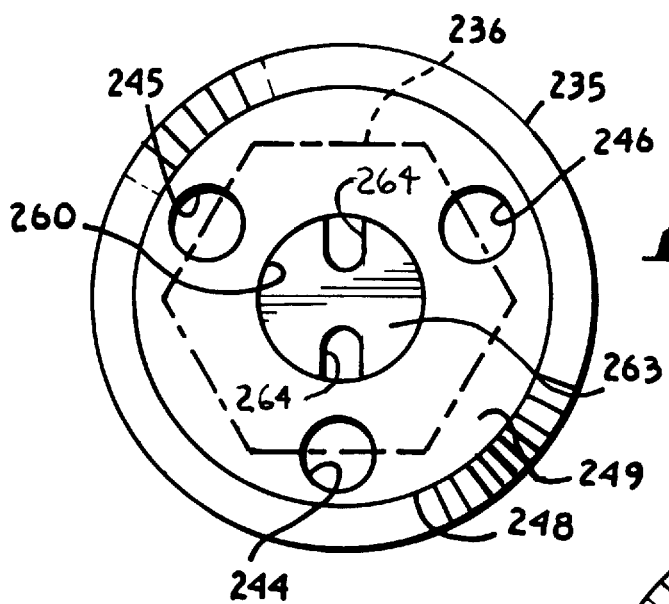
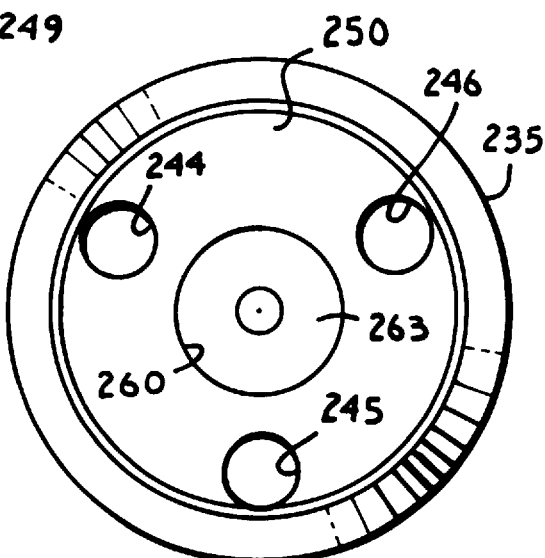

THREADED CLOSURE WITH INWARDLY-FACING TOOL ENGAGING CONCAVE RADIUSED STRUCTURES AND AXIAL THROUGH-APERTURE

CROSS REFERENCE TO RELATED APPLICATIONS

The present application is a continuation of U.S. application Ser. No. 16/016,212, filed Jun. 22, 2018, which is a continuation of U.S. application Ser. No. 15/883,993, filed Jan. 30, 2018, now U.S. Pat. No. 10,004,541, which is a continuation of Ser. No. 15/144,915, filed May 3, 2016, now U.S. Pat. No. 9,907,577, which is a continuation of U.S. application Ser. No. 14/509,496, filed Oct. 8, 2014, now abandoned, which is a continuation of U.S. application Ser. No. 13/694,970, filed Jan. 23, 2013, now abandoned, which is a continuation of U.S. application Ser. No. 10/142,614, filed May 9, 2002, now U.S. Pat. No. 8,377,100, which is a continuation-in-part of U.S. application Ser. No. 10/014,434 filed Nov. 9, 2001, now U.S. Pat. No. 6,726,687, each of which is fully incorporated by reference herein for all purposes.

BACKGROUND OF THE INVENTION

The present invention is directed to an open headed medical implant and, in particular, to a closure for closing the head of an open headed bone screw, hook or the like.

Bone screws are used especially in spinal surgery to support and position various implants needed to repair a spine that has suffered injury, illness or genetic defect. Bone screws of this type are screwed into the vertebra of the spine and have a head that projects outside the bone which receives other implants, such as rods, that extend along the spine. Bone screws are of two general types which are either open headed or closed headed. Hooks and certain other implants also sometimes have open heads. The present application is directed to open headed bone screws and related implants such as hooks and the like that have such an open head to receive another implant.

In open headed bone screws and related implants, the head includes two upright arms that form a channel therebetween. The channel is sized to receive a rod or the like and is open to make it easier to place the rod in the head. The rod must then be tightly held or locked in the head to prevent relative movement between implants after the surgery. To hold the rod in the head, plugs have been used that are screwed into threads on the interior surfaces of the arms.

The present invention is directed especially to improvements in such plugs or closures that make them easier to insert in the head, that better ensure that the plug effectively secures the rod so that the rod does not later slip, that allow the plugs to be easily removed should the overall implant system require rearrangement and which provide a comparatively low profile, so as reduce trauma and irritation to the surrounding tissues of the patient.

SUMMARY OF THE INVENTION

A closure is provided for an open headed implant, especially a bone screw or hook for use in spinal surgery. The closure has a cylindrical shaped body with an axis of rotation. The body has a radially outer surface that has a thread or other guide and advancement structure thereon that is sized and shaped to be received in mating threads or structure on interior surfaces of arms of the implant head. The closure is operably rotated and advanced into the head of the implant to capture a rod or other part of an overall spinal support system. The closure captures and locks such a rod in position relative to the implant to prevent rotation or axial movement between the joined parts.

The closure body has a top surface and a bottom surface with a plurality of cylindrical bores extending parallel to the axis of rotation into the body from the top surface or other removal apertures. The bores or apertures are positioned in spaced relationship to one another and to the axis of rotation. The bores or apertures are sized and shaped to cooperatively mate with posts on a tool to allow removal of the closure from the implant after insertion, should such be necessary.

The closure also includes a break-off head centrally mounted by a neck on the top surface of the body. The break-off head is adapted to receive a socket tool and be rotated thereby during installation. The break-off head is also designed to break from the body at a torque limiting or break-off region or location which is preferably whereat the neck intersects with the top surface of the body, when a preselected torque is applied to the break-off head. When the break-off head is broken away, the bores or apertures become exposed and are mateable with a removal tool should it become necessary to remove the closure.

In a second embodiment the body includes a central threaded bore that receives a set screw. The body is then used for capture of a rod or the like and the set screw is used to lock the rod or the like in position relative to the implant.

In a third embodiment, a body includes both a break-off head and a central threaded bore that is covered by the break-off head until the head breaks away, after which the threaded bore is exposed at the top surface of the body to receive a set screw.

OBJECTS AND ADVANTAGES OF THE INVENTION

Therefore, the objects of the present invention are: to provide a closure for an open ended implant that provides a plurality of spaced removal apertures that are offset from an axis of rotation of the closure and that cooperate with a tool to allow removal of the closure; to provide such an implant having a closure with a break off head for mating with an insertion tool for inserting the closure into the implant; to provide such an implant wherein the removal apertures are not accessible for effective access, when the closure is in the implant until the break-off head is broken away; to provide such an implant that strongly grips a rod or the like received in the implant and that provides a relatively low profile; and to provide such an implant and closure therefor that is relatively easy to use, comparatively easy to produce and is especially well suited for the intended use thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a bone screw type implant and closure in accordance with the present invention prior to insertion of the closure into a head of the bone screw.

FIG. 2 is a fragmentary side elevational view of the bone screw with a rod and the closure received therein and with a tool being utilized to insert the closure and provide torque to the break-off head of the closure and further with the bone screw shown embedded in a bone that is indicated by phantom lines.

FIG. 3 is a fragmentary and exploded side elevational view of the bone screw, rod and closure with the break-off head of the closure being shown broken therefrom.

FIG. 4 is a fragmentary top plan view of the bone screw, rod and closure with the break-off head removed.

FIG. 5 is a top plan view of the closure with the break-off head broken therefrom, but shown in phantom.

FIG. 6 is a bottom plan view of the closure.

FIG. 7 is an exploded and fragmentary side elevational view of the bone screw, rod and closure showing a removal tool positioned above the closure.

FIG. 8 is a fragmentary and enlarged view of the bone screw, rod and closure shown in FIG. 7 with the removal tool inserted into the closure and with portions of the bone screw and closure broken away to show detail thereof.

FIG. 9 is an exploded perspective view of a modified bone screw and closure in accordance with the present invention, also showing a rod received in a head of the bone screw in phantom lines and a tool for use in inserting the closure into and removing the closure from the head of the bone screw.

FIG. 14 is a side elevational view of a closure in accordance with a third modified embodiment of the present invention.

FIG. 15 is a top plan view of the closure of the third modified embodiment with a break-off head thereof broken away.

FIG. 16 is a bottom plan view of the closure of the third modified embodiment of the invention.

DETAILED DESCRIPTION OF THE INVENTION

Figure 10:
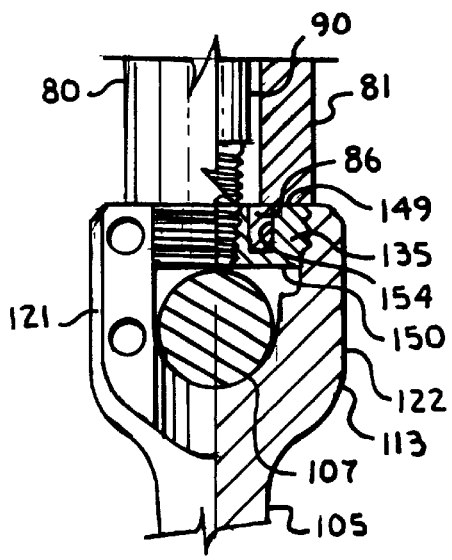
FIG. 10 is a side elevational view of the bone screw, rod, closure and tool of the second embodiment of the invention with portions broken away to show internal detail thereof.
Figure 11:
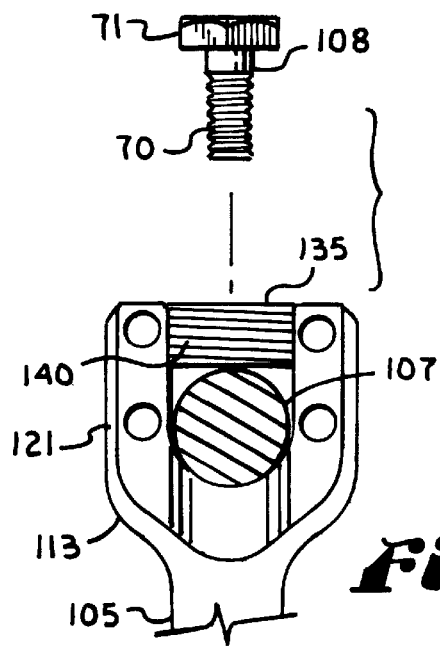
FIG. 11 is a fragmentary side elevational view of the bone screw, rod and closure also showing a set screw that is positioned to be received in the closure.
Figure 12:
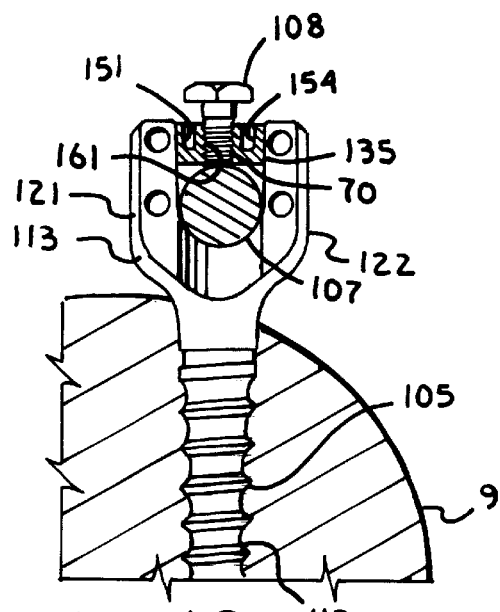
FIG. 12 is a fragmentary side elevational view showing the bone screw, rod, closure and closure set screw positioned in a vertebra that is shown in cross-section.
Figure 13:
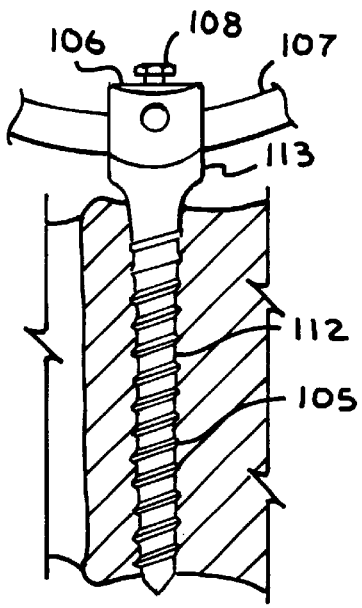
FIG. 13 is a front elevational view of the bone screw, rod and closure shown mounted in a vertebra that is shown in cross-section.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference numeral 1 generally indicates a medical implant in accordance with the present invention. The implant 1 includes a bone screw 5, a closure 6 for the bone screw 5 and a rod 7. The implant 1 is received in a vertebra 9, typically in conjunction with other implants that are not shown. The closure 6 also functions in conjunction with other open-headed implants, such as hooks and the like.

The bone screw 5 includes a shank 12 and a head 13. The shank 12 is threaded with a coarse helically wound thread 16 that is threaded into the vertebra 9, so as to secure and support the bone screw 5 and allow the head 13 to extend from the vertebra 9.

The bone screw head 13 includes a base 20 with a pair of upstanding spaced arms 21 and 22 on opposite sides of the base 20 forming a generally U-shaped configuration, when viewed from the side, and defining a channel 23 therebetween. The channel 23 is sized and shaped to receive the rod 7.

The arms 21 and 22 each include an interior surface 26 and 27, respectively. The interior surfaces 26 and 27 have a guide and advancement structure which in the illustrated embodiment is a partial helical wound thread 29 on each. While the illustrated thread 29 is a conventional V-shaped thread, the purpose of this thread is to engage similar threads on the closure 6 to guide the closure 6 relative to the bone screw 5, as discussed below, and to provide for biased advancement of the closure 6 along the central axis A thereof relative to the bone screw 5 upon rotation of the closure 6. It is foreseen that other structures including other types of threads, such as buttress and reverse angle threads, and non threads, such as helical wound flanges or the like having interlocking surfaces, could be alternatively used for this purpose. Therefore, the illustrated internal partial or discontinuous threads on the bone screw arms 21 and 22 along with the mating thread on the closure 6 provide guide and advancement structure that operably positions and advances the closure 6 relative to the bone screw 5 during installation. The threaded surfaces 26 and 27 are spaced and not connected so as to present only a partial threadform which each face one another and cooperate with the closure 6, as is noted below. In the illustrated embodiment, the threaded surfaces 26 and 27 extend from a top 30 of the bone screw 5 only partially down the arms 21 and 22.

The closure 6 includes a body 35 and a torque limiting break-off head 36. The closure body 35 is generally cylindrical in shape and has a radially outward external surface 40 that extends 360° about an axis of rotation indicated by the reference letter "A". In the present embodiment, the surface 40 has a portion of the mating guide and advancement structure thereon which in the illustrated embodiment is a thread 41 that mates with the partial thread 29 on the bone screw 5 and biases the closure 6 forward due to interaction of the threads 29 and 41 upon clockwise rotation of the closure 6. As noted before, this function can be provided by alternative types of threads or other non threaded structures such as a helically wound flange that slidably mates with a similar structure on the bone screw 5. In the illustrated embodiment the threaded surface 40 has a threadform located thereon that entirely encircles the outer surface 40 of the body 35 and extends entirely from top to bottom. The surface 40 is provided with a thread 41 that is sized, shaped and configured to threadably mate with the threaded surfaces 26 and 27 of the arms 21 and 22, so that the closure body 35 may be threaded into the bone screw head 13, as is shown in FIG. 2.

The closure body 35 also includes at least one removal aperture and in the illustrated embodiment such an aperture is provided by three bores 44, 45 and 46 that are aligned to be parallel with the axis of rotation. The bores 44, 45 and 46 are spaced both from the axis of rotation A and from a periphery 48 of a top 49 of the body. The bores 44, 45 and 46 extend from the body top 49 to a bottom surface 50 of the body 35 in the illustrated embodiment. Preferably the bores 44, 45 and 46 are equally spaced from one another and are approximately equally radially spaced outward from the axis of rotation A. In the illustrated embodiment, the bores 44, 45 and 46 are spaced at approximately 120° from one another. While three cylindrical bores are shown and function as the removal aperture in the illustrated embodiment, it is foreseen that various numbers of openings could be equivalently used and/or such apertures may be of various shapes, such as round, square or kidney bean in cross section, and may be pass through from top 49 to bottom surface 50 of the closure 6 or may just pass through the top 49 thereof and extend partially therethrough.

The break-off head 36 includes a neck 54 that joins with the body top 49 at a torque limiting region or break-off location 56. Preferably the break-off location 56 is generally coplanar with the body top 49, so the break-off location 56 is clean and low profile after such breakoff. The break-off location 56 is normally determined by the location whereat the neck 54 is smallest in cross-section or the location 56 can be triggered by an external groove and other devices known for this purpose. The neck 54 also converges somewhat from the remainder of the break-off head 36 to the break-off location 56.

The break-off head 36 includes a number of facets or panels 60 which are aligned to be parallel to the axis of rotation A and which are joined together to form a polyhedral shaped surface 61 typically associated with a structure to be received in a socket-type tool. The combined surface 61 of the facets 60 forms such a polyhedral shape. A top surface 63 of the break-off head 36 has axially located therein a non-threaded bore 65 for operably receiving a tool during implantation. The bottom surface 50 of the body 35 includes a conical shaped and axially aligned point 67 for engaging and preferably biting into the rod 7, so as to provide an improved grip on the rod to prevent rotation or axial movement thereof relative to the bone screw 5. It is foreseen that the bottom surface 50 may be flat or otherwise shaped and may include other structure to increase frictional engagement between the closure 6 and the rod 7, such as: knurling; a ring with a sharp lower edge, especially when used in conjunction with and surrounding the point 67; or the like.

A tool 70 is illustrated in FIG. 2 for cooperatively inserting the closure 6 into the bone screw head 13. The tool 70 has an elongate shank 71 with a handle 72 sized and shaped to allow a user to rotate the tool 70 clockwise about the axis of rotation A associated with the closure 6. The tool 70 also has a socket type head 74 opposite the handle 72 that is sized and shaped to snugly receive the outer surface 61 of the break off head 36 as is shown in FIG. 2.

During assembly, the rod 7, which is elongate and generally circular in cross-section, is placed within the bone screw channel 23 and the closure 6 is then threaded into the bone screw head 13. The tool 70 is used to rotate the closure 6 until it engages the rod 7 and urges the rod 7 to seat tightly and snugly on the bone screw head base 20 at the bottom of the channel 23. The point 67 engages and digs into the rod 7. As additional torque is applied to the tool 70, a preselected torque is eventually reached (for example 90 inch pounds) whereat the break-off head 36 breaks from the closure body 35 at the break-off location 56 and separates therefrom, such as is shown in FIG. 3.

FIGS. 3 and 4 illustrate the closure 6 operably positioned within the bone screw head 13. FIG. 5 illustrates the closure 6 with the break-off head 36 removed, but shown in phantom to illustrate the position of the break-off head 36 relative to the bores 44, 45 and 46.

In certain circumstances, it is necessary to remove the closure 6 to readjust the position of the rod 7 or to make some other change in the implant 1 configuration. As mentioned before, the implant 1 is typically a part of an overall system and is normally used to provide support to damaged, injured or missing vertebra of the spinal column. When it is necessary to readjust the overall system, the closure 6 is removed by utilization of the second tool 78. The tool 78 includes a shank 80 that has an axis of rotation during use that is coaxial with the axis of rotation A of the closure 6. The shank 80 is attached at one end to a handle 81 to provide a grasp and a means of turning the tool 78 by a user. Opposite the handle 81, the shank 80 has a flat surface 83 from which three pegs or posts 84, 85 and 86 project.

The posts 84, 85 and 86 are parallel to the axis of rotation of the tool 78 and are sized, shaped and positioned so as to be snugly receivable in the closure bores 44, 45 and 46, subsequent to removal of the break-off head 36. The tool 78 is shown in position above the closure body 35 in FIG. 7 just prior to insertion of the posts 84, 85 and 86 into respective bores 44, 45 and 46. The tool 78 is shown positioned with the posts 84, 85 and 86 in the respective bores 44, 45 and 46 in FIG. 8. The purpose of the tool 70 is to allow a user to rotate the closure body 35 counter-clockwise and remove the body 35 from the bone screw head 13 after the closure 6 has been seated therein. In this way the channel 23 can be reopened and the rod 7 removed or repositioned relative to the bone screw head 13.

While the non-axially located bores 44, 45 and 46 of the present embodiment are located between the break-off head neck 54 and the periphery 48, it is foreseen that one or more non-axial bores of this type could partially or entirely intersect with the neck 54 so as to become fully open or exposed at the closure top surface 49 only when a break-off head associated with such a neck breaks from the closure body.

Illustrated in FIGS. 9 to 13 is second embodiment or first modified embodiment of an implant in accordance with the present invention that is generally identified by the reference numeral 101. The implant 101 includes a bone screw 105, a closure 106, a rod 107 and a set screw 108.

The bone screw 105 except for the closure is essentially the same as the bone screw 5 and, therefore, will not be described in detail. Reference is made to the description of bone screw 5 for additional detail. The bone screw 105 has a shank 112 and a head 113. Upright arms 121 and 122 of the head 113 have inner or interior facing and threaded surfaces 126 and 127.

The rod 107 is elongate and has a generally circular cross section for being received in the head 113 beneath the closure 106.

The closure 106 is similar in some respects to the closure 6, but is installed in a different manner. In particular, the closure 106 has a generally cylindrical shaped body 135 that has a threaded radially outward surface 140 that has a thread thereon that is sized, shaped and positioned to threadedly mate with threads of the arm threaded surfaces 126 and 127, as seen in FIG. 10. The thread can be a conventional V-thread, a buttress thread, a reverse angle thread or other threads related to reverse angle threads in that they exert forces to draw or pull the arms 121 and 122 toward one another rather than cause them to splay or open at the top.

The body 135 also has a top surface 149 and a bottom surface 150. Positioned to extend downwardly into the body 135 from the top surface 149 are four equally spaced bores 151, 152, 153 and 154 that do not extend entirely through the body 135 from top to bottom. The bores 151, 152, 153 and 154 are spaced from and positioned between both a central axis B and a periphery 158 of the body top surface 149. Each bore 151, 152, 153 and 154 is positioned at approximately 90° relative to adjacent bores 151, 152, 153 and 154.

Located axially and centrally in the body 135 is a threaded bore 161. The threaded bore 161 extends between the top surface 149 and bottom surface 150.

The set screw 108 has a threaded shaft 170 sized and shaped to be threadably received in the body threaded bore 161. The set screw 170 has sufficient length to extend through and outward from the bottom surface 150. In the second embodiment the set screw 108 has a head 171 that is grippable by a tool for rotation and torquing. The closure 6 and the closure 106 are interchangeable.

A tool 180 is provided for installing and removing the closure 106 from the bone screw head 113. The tool 180 is T-shaped having a shank 181 with a handle 182 attached to one end and a generally flat surface 184 at an opposite end. The surface 184 has four pegs or posts 186 extending therefrom. The posts 186 extend from the surface 184 parallel to an axis of rotation of the tool 180 which is the same in use as the axis of rotation B of the closure. The posts 186 are aligned, sized and shaped to mate with the closure body bores 151, 152, 153 and 154.

The tool shank 180 also includes an axial bore extending therethrough and receiving a keeper rod 190. The rod 190 has a threaded tip 191 that is adapted to be received in the closure body bore 161 and a grasping head 192 at an opposite end.

In use the rod 107 is placed in the head 113 and the tool 180 is mated with the closure 106 in the manner shown in FIG. 10, so that the four posts 186 are located in respective bores 151, 152, 152 and 154 and the rod tip 191 is threaded into the threaded bore 161. The closure 106 is then mated with the head 113 and threaded thereon by mating of the surface 140 with the arm surfaces 126 and 127 until the closure 106 is snug in the bone screw head 113. Torque in a preselected amount is applied to the closure 106 to ensure it is tightly seated in the head 113. In some instances, the closure 106 may just be used to capture the rod 107 and the set screw 108 is used to lock the rod 107 in place. In particular, the tool 180 may be removed and the set screw 108 is then placed in the bore 161 and advanced against the rod 107. A preselected torque is applied to lock the rod 107 in a selected position in the head 113.

It is foreseen that the set screw 108 may be of other types than the one illustrated. That is the set screw could have a break-off head in which case the overall implant 101 would have a comparatively low profile associated with only the top of the bone screw.

For removal, the installation process is reversed. That is the tool 180 is utilized to rotate the closure 106 counter-clockwise rather than the clockwise direction used for inserting. Where a break off set screw is used, the set screw can be rotated with the body 135 of the closure 106 for removal.

Illustrated in FIGS. 14, 15 and 16 is a third embodiment or second modified embodiment of a bone screw closure in accordance with the present invention and generally identified by the reference numeral 206.

The closure 206 is in many ways similar to the closure 6 and reference is made to the disclosure for the closure 6 for additional detail.

In particular the closure 206 has a generally cylindrically shaped body 235 that has a radially outer threaded surface 240. The closure 235 also has a break-off head 236 secured to a top or upper surface 249 of the body 235 by a neck 254 at a break-off location 256. Positioned between the neck 254 and a periphery 248 of the body upper surface 249 are three bores 244, 245 and 246 that extend parallel to a central axis of rotation identified by a reference numeral C.

The major difference between the present embodiment and the closure 6 shown in the first embodiment is that a body 235 thereof also includes a central or axial bore 260 extending from a bottom surface 250 upward through the body 235 to the level of an upper surface 249 of the body 235. The bore 260 is threaded and covered by the neck 254 until the break-off head 236 breaks from the body 235 during installation by application of torque, as was described in the first embodiment. The bore 260 is thereafter exposed upwardly or at the upper surface 249 and adapted to receive a set screw 263 of the type used in the second embodiment or alternatively a break-off type, as shown, set screw having removal slots 264. It is noted that the diameter of the neck 254 at the top surface 249 is larger than the diameter of the bore 260.

It is to be understood that while certain forms of the present invention have been illustrated and described herein, it is not to be limited to the specific forms or arrangement of parts described and shown. The same screw head and rod can be locked by any of the three closure embodiments as described above.

What is claimed and desired to be secured by Letters Patent is as follows:

1. A medical implant assembly configured for attachment to a bone of a patient, the assembly comprising:
   an elongate rod having a cylindrical shape;
   a bone anchor head including a first upright arm having a first top surface, a first exterior surface adjacent to the first top surface, and a first interior surface;
   a second upright arm having a second top surface, a second exterior surface adjacent to the second top surface, and a second interior surface;
   a discontinuous helically wound thread extending along at least a portion of the first and second interior surfaces;
   a channel formed between the first upright arm and the second upright arm, the channel configured to receive the rod;
   a closure having a central axis and comprising a closed body with a planar top body surface opposite a bottom body surface and a thickness defined between the top body surface and a most distal portion of the bottom body surface, a central through-opening extending from the planar top body surface to the bottom body surface, a cylindrical outer body surface at least a portion of which having a helically wound thread extending radially therefrom and configured to limit the first and second upright arms from splaying, at least three spaced-apart tool mating structures formed in the closed body, the tool mating structures being equally angularly spaced apart from each other at an equal radial distance with respect to the central axis of the closure, each tool mating structure being at least partially defined by a bore hole extending below the top body surface, the bore hole being a portion of a passageway between the bottom body surface and the top body surface of the closed body and including an inwardly-facing surface extending parallel relative to the central axis, the central through-opening including at least a partial cylindrical inwardly-facing surface extending parallel relative to the central axis between the top and bottom body surfaces, the tool mating structure inwardly-facing surface having a radius of curvature that is less than the radially farthest distance between the respective inwardly-facing surface and the central axis of the closure;

the helically wound thread extending about at least the portion of the cylindrical outer body surface, the helically wound thread configured to threadedly mate with the discontinuous helically wound thread during rotational advancement of the closure within the channel to thereby close the channel and capture the rod such that when the helically wound thread of the closed body is fully mated with the discontinuous helically wound thread of the bone anchor head, the first top surface, the second top surface, the first exterior surface, and the second exterior surface are each completely not covered by the closure when the rod is locked within the channel of the bone anchor head by the closure; and the bottom body surface of the closed body of the closure having an inner continuous edge surrounding a lower portion of the central through-opening and an outer continuous edge surrounding and radially spaced apart from the inner continuous edge, at least a portion of the inner continuous edge or the outer continuous edge and a portion of the bottom body surface therebetween configured to engage and compress the rod into a locked position within the channel of the bone anchor head, wherein the inwardly-facing surface of each tool mating structure extends between the planar top body surface of the closed body of the closure and the bottom body surface of the closed body of the closure so as to be radially inset from the helically wound thread of the cylindrical outer body surface along an entire length of the inwardly-facing surface of each tool mating structure.

2. The medical implant assembly of claim 1, wherein the helical wound thread on the outer body surface is configured as a buttress thread.

3. The medical implant assembly of claim 1, wherein the central through-opening is threaded.

4. The medical implant assembly of claim 1, wherein the inwardly-facing surfaces of the at least three tool mating structures are configured to be engageable by a tool when at least a portion of the tool is receivable within at least one or more of the tool mating structures to thereby rotate the closure with respect to the first and second upright arms.

5. The medical implant assembly of claim 1, wherein at least a portion of the central through-opening is configured as a closed bore hole aperture spaced apart from at least a most outwardly positioned portion of the inwardly-facing surface of each tool mating structure facing the central axis.

6. The medical implant assembly of claim 1, wherein the outer continuous edge has a same diameter as the cylindrical outer body surface.

7. A medical implant assembly comprising:
a bone anchor head including a first upright arm and a second upright arm, the first upright arm having a first top surface, a first exterior surface adjacent to the first top surface, and a first interior surface, the second upright arm having a second top surface, a second exterior surface adjacent to the second top surface, and a second interior surface;

a channel formed between the first upright arm and the second upright arm, the channel configured to receive a rod;

a discontinuous helically wound thread extending along at least a portion of the first interior surface and the second interior surface;

a closure having a longitudinal axis and comprising a closed body having a top body surface opposite a bottom body surface, a central through-opening formed around the longitudinal axis and extending between the top body surface and the bottom body surface, a cylindrical outer body surface with a helically wound thread extending radially therefrom and configured to limit the first and second upright arms from splaying, at least three spaced-apart tool mating structures formed in the closed body and equally angularly spaced apart from each other an equal radial distance with respect to the longitudinal axis of the closure, at least a portion of each tool mating structure configured as at least partial bore hole apertures, the central through-opening having an inwardly-facing surface at least a portion of which is cylindrical in shape, the tool mating structures each having inwardly-facing surfaces that are concave in shape with a radius of curvature equal to each other extending from and around the longitudinal axis of the closure;

the helically wound thread extending about the cylindrical outer body surface, the helically wound thread configured to threadedly mate with the discontinuous helically wound thread during rotational advancement of the closure within the channel to thereby close the channel and capture the rod such that when the helically wound thread of the closed body is fully mated with the discontinuous helically wound thread of the bone anchor head, the first top surface, the second top surface, the first exterior surface, and the second exterior surface are each completely not covered by the closure when the rod is locked within the bone anchor head by the closure; and the bottom body surface of the closed body of the closure configured to engage and compress the rod into a locked position within the channel of the bone anchor head, wherein the inwardly-facing surfaces of the at least three tool mating structures are configured to be engageable by a lower portion of a tool when the tool engages the inwardly-facing surfaces thereof to thereby rotate the closure with respect to the first and second upright arms; and wherein each of the inwardly-facing surfaces of the at least three tool mating structures forms a portion of a passageway between the top body surface and the bottom body surface of the closed body.

8. The medical implant assembly of claim 7, wherein the top body surface and the bottom body surface are planar surfaces parallel with respect to each other and perpendicular with respect to the longitudinal axis of the closure.

9. The medical implant assembly of claim 7, wherein the central through-opening extends to a lower opening adjacent to the bottom body surface and communicates with a circular inner edge formed on the bottom body surface of the closed body of the closure and at least a portion of the circular inner edge is configured to engage and compress the rod into a locked position within the channel of the bone anchor head.

10. The medical implant assembly of claim 7, wherein the tool mating structures are spaced apart from the outer body surface of the closed body of the closure.

11. The medical implant assembly of claim 7, wherein the central through-opening is threaded.

12. The medical implant assembly of claim 7, wherein each inwardly-facing surface of the at least three tool mating structures extends down into the closed body an equal distance.

13. The medical implant assembly of claim 7, wherein at least a portion of the central through-opening is configured as a closed bore hole aperture spaced apart from the tool mating structures.

14. The medical implant assembly of claim 7, further including the rod.

15. The medical implant assembly of claim 7, wherein the bottom body surface of the closed body of the closure has a circular outer edge configured to engage and compress the rod into a locked position within the channel of the bone anchor head and the circular outer edge has a diameter equal to a diameter of the cylindrical outer body surface.

\* \* \* \* \*